United States Patent
Eckert (10) Patent No.: US 6,752,153 B1
(45) Date of Patent: Jun. 22, 2004

(54) INHALATOR COMPRISING A DOSAGE COUNTING DEVICE

(75) Inventor: Joseph Eckert, Mellrichstadt (DE)

(73) Assignee: RPC Wiko GmbH & Co. KG, Pulheim (DE)

( * ) Notice: Subject to any disclaimer, the term of this patent is extended or adjusted under 35 U.S.C. 154(b) by 0 days.

(21) Appl. No.: 09/762,899

(22) PCT Filed: Aug. 13, 1999

(86) PCT No.: PCT/EP99/05939

§ 371 (c)(1),
(2), (4) Date: Apr. 2, 2001

(87) PCT Pub. No.: WO00/09187

PCT Pub. Date: Feb. 24, 2000

(30) Foreign Application Priority Data

Aug. 14, 1998 (DE) ..................... 298 14 647 U (51) Int. Cl.$^7$ ............................. A62B 7/00; A62B 9/00
(52) U.S. Cl. ........................... 128/205.23; 128/203.12; 128/200.23
(58) Field of Search ................. 128/200.23, 203.12, 128/203.15, 205.23; 222/36, 38, 48

(56) References Cited

U.S. PATENT DOCUMENTS

| | | | | |
|---|---|---|---|---|
| 184,616 A | * | 11/1876 | Harper | 222/36 |
| 386,695 A | * | 7/1888 | Ehlers | 222/38 |
| 3,085,745 A | * | 4/1963 | Auberger | 222/36 |
| 3,655,952 A | * | 4/1972 | Johnson et al. | 235/94 R |
| 4,565,302 A | * | 1/1986 | Pfeiffer et al. | 222/38 |
| 4,817,822 A | * | 4/1989 | Rand et al. | 222/38 |
| 5,174,473 A | * | 12/1992 | Marelli | 222/38 |
| 5,349,945 A | * | 9/1994 | Wass et al. | 128/200.23 |
| 5,421,482 A | * | 6/1995 | Garby et al. | 222/36 |
| 5,482,030 A | * | 1/1996 | Klein | 128/200.23 |
| 5,544,647 A | * | 8/1996 | Jewett et al. | 128/200.23 |
| 5,564,414 A | * | 10/1996 | Walker et al. | 128/200.23 |
| 5,611,444 A | * | 3/1997 | Garby et al. | 215/230 |
| 5,687,710 A | * | 11/1997 | Ambrosio et al. | 128/203.15 |
| 5,718,355 A | * | 2/1998 | Garby et al. | 222/36 |
| 5,740,792 A | * | 4/1998 | Ashley et al. | 128/203.15 |
| 5,799,651 A | * | 9/1998 | Garby et al. | 128/200.23 |
| 5,829,434 A | * | 11/1998 | Ambrosio et al. | 128/203.15 |
| 5,988,496 A | * | 11/1999 | Bruna | 235/91 R |
| 6,076,521 A | * | 6/2000 | Lindahl et al. | 128/203.15 |
| 6,082,358 A | * | 7/2000 | Scarrott et al. | 128/205.23 |
| 6,142,339 A | * | 11/2000 | Blacker et al. | 222/23 |
| 6,234,168 B1 | * | 5/2001 | Bruna | 128/203.12 |
| 6,240,918 B1 | * | 6/2001 | Ambrosio et al. | 128/203.15 |
| 6,328,037 B1 | * | 12/2001 | Scarrott et al. | 128/205.23 |
| 6,435,372 B1 | * | 8/2002 | Blacker et al. | 222/23 |
| 6,446,627 B1 | * | 9/2002 | Bowman et al. | 128/200.23 |

FOREIGN PATENT DOCUMENTS

| | | |
|---|---|---|
| EP | 0480488 | 4/1992 |
| EP | 0949584 | 10/1999 |
| FR | 2022212 | 7/1970 |
| WO | 9414492 | 7/1994 |
| WO | 9629278 | 9/1996 |

* cited by examiner

Primary Examiner—Aaron J. Lewis
Assistant Examiner—Joseph F Weiss, Jr.
(74) Attorney, Agent, or Firm—Friedrich Kueffner (57) ABSTRACT

The invention is an inhaler for aerosolization of medicament with a unique dosage counter. The dosage counter has a first and second counting ring and a coupling device that interconnects the counting rings. The counter being advanced by a unique armature mechanism that is interconnected with the actuation mechanism of the inhaler to insure accurate counting of doses.

22 Claims, 7 Drawing Sheets

INHALATOR COMPRISING A DOSAGE COUNTING DEVICE

BACKGROUND OF THE INVENTION

1. Field of the Invention

The invention relates to an inhalator for dispensing an aerosol comprising a dosage counting device, a housing part, and an aerosol dispensing container displaceably arranged relative to the housing part along its longitudinal axis.

2. Discussion of the Relevant Art

Such an inhalator is known from EP-A1-0 254 391. In these conventional inhalators, an aerosol dispensing container is displaceably inserted into a tubular portion of a housing part. The dispensing container comprises a spraying tube which is guided out of a head area of the dispensing container, which spraying tube is inserted in a sealed manner into a spraying socket portion which is formed as a monolithic part of the housing. For dispensing a predetermined dosage of the medium stored in the dispensing container, a pressure force is applied to a bottom portion of the dispensing container and the container is briefly forced into the housing. Via the spraying tube inserted into the spraying socket a valve mechanism is opened for a moment and a predetermined amount of the medium contained in the storage container is sprayed via the spraying head. In a lateral area of the housing an indicator wheel is provided which is rotatably supported and which is rotated farther for each dispensing stroke of the inhalator by means of a step-down gear system by a minimal rotational distance. The indicator wheel is provided with several filling level indicating marks which can be read by means of a window portion for a successive rotation of the indicator wheel. When the dispensing container is almost completely emptied, a corresponding symbol is visible in the window, and this signalizes to the user that the dispensing container is substantially completely empty. By means of overfilling of the dispensing container at the manufacturing site by approximately 10 to 15%, it is ensured that upon reaching this end mark a sufficient amount of active substance is still stored in the dispensing container.

The overfilling of the dispensing container carried out at the manufacturing site, in particular, when filling with comparatively expensive active substances, results in an increase in cost of the inhalator. Also, with regard to environmental protection considerations an overfilling of the dispensing container to the degree that has been conventional up to now appears to be problematic.

SUMMARY OF THE INVENTION

The invention has therefore the object to provide an inhalator for dispensing aerosols which is characterized by a high functional reliability and a dosage counting device improved with respect to readability and indication precision.

This object is solved according to the invention by an inhalator having a first counting ring which is arranged coaxially to the longitudinal axis of the aerosol dispensing container and is rotatable about this longitudinal axis; a second counting ring which is arranged coaxially to the first counting ring and can be directly coupled therewith and is rotatable relative thereto; counting ring switching device for rotation of the first counting ring upon actuation of the inhalator; and a coupling device for coupling the second counting ring with the first counting ring for a stepwise rotation of the second counting ring together with the first counting ring; wherein the counting ring switching device has an actuation portion and a switching finger coupled therewith, which for rotation of the corresponding counting ring can be brought into engagement with control elements thereof.

In this way, it is possible in an advantageous manner to provide an inhalator which can be produced with respect to manufacturing technological aspects in a beneficial way and with which, as needed, each individual dosage stroke is counted and indicated. In addition to the thus obtained reliable monitoring of residual filling amounts of the active substance medium stored in the inhalator, it is moreover possible to monitor the administration of the dosage aerosols in correspondence with the prescription in an improved way. The inventively embodied dosage counting device makes possible, for example, counting from 0 to approximately 200 of the individual dosage amounts. As an alternative to this, it is also possible to provide the number arrangement on the two counting rings such that dosage counting is possible in a descending order starting at the maximum stroke number. Counting can be performed successively in the descending order, for example, starting with the number 200, wherein, for example, when the residual stroke number is ≦50, in the indicator device a color marking, for example, in the form of a signaling bar, becomes visible which signalizes to the respective user in a timely fashion that a new inhalator must be obtained.

The improvement of the indicating precision possible with the dosage counting device according to the invention makes it possible to reduce the overfilling of the dispensing container, performed for safety reasons, and to thus reduce the residual amount of active substance in the dispensing container.

An advantageous embodiment of the invention with respect to a particularly reliable further switching of the first counting ring is provided in that the switching finger is spaced from the rotational axis and is positioned at a slant thereto. Accordingly, it is possible in a kinematically beneficial way to bring the switching finger into engagement with control elements provided at the counting ring and to tilt the switching finger subsequently about a tilting axis which extends substantially transversely to the longitudinal direction of the switching finger. The positioning angle of the switching finger relative to a radial plane defined by the counting ring is preferably in the range of 30 to 60°. In this connection, sufficiently large transport paths of the switching fingers result in connection with favorable force ratios.

According to a preferred embodiment of the invention, the switching finger can be deflected out of an initial position into an end position which is slanted relative to the initial position, wherein an engagement portion of the switching finger is forced already in the initial position thereof in an elastically yielding fashion into an engagement position with the first counting ring. Accordingly, in a reliable way it is ensured that each individual dispensing stroke of the inhalator is counted by the dosage counting device.

An advantageous embodiment of the invention with respect to an especially beneficial conversion of the dispensing stroke of the dispensing container of the inhalator into a further switching movement required for operating the dosage counting device is provided in that an arm part is provided that is coupled with the switching finger wherein the arm part and the switching finger form an elbow joint mechanism. This ensures for still advantageous force ratios a comparatively long switching finger transport distance so that it is possible to space the numbers provided on the first counting ring so far apart from one another that only one individual number of the counting ring is visible within the window portion, respectively.

The return force required for returning the switching finger can be provided in an advantageous way by elastic deformation of the switching finger or of the actuator elements which are coupled with the switching finger. The switching finger is comprised advantageously of a plastic material, preferably a thermoplastically formable plastic material.

An advantageous embodiment of the invention with respect to a reliable actuation of the switching finger is provided in that the arm part and the switching finger are connected to one another by means of an actuation portion. The actuation portion forms in an advantageous way a contact surface facing a shoulder portion of the dispensing container of the inhalator, which contact surface, upon lowering of the dispensing container within the context of a dosage stroke, is deflected from its initial position, in particular, is moved substantially in the axial direction of the dispensing container.

The arm part and the switching finger are formed as a monolithic part according to a preferred embodiment of the invention. Advantageously, in this embodiment the actuation portion is provided in the connecting area between the arm part and the switching finger. The movability of arm part and switching finger relative to one another results substantially from the elasticity of the material in the area of the corresponding transition locations. The geometry of the transition portions is selected such that at least in the context of the determined number of dosage strokes no considerable material fatigue or cross-sectional weakness is caused in the corresponding connecting portions.

An advantageous embodiment of the invention with respect to an especially high functional reliability of the dosage counting device is provided in that at least the first counting ring, preferably also the second counting ring, and in a particularly advantageous way also the switching finger are made of POM. The remaining components of the inhalator can be made of comparatively inexpensive plastic materials, such as, for example, polystyrene or polyethylene or other, preferably thermoplastically deformable, plastic materials.

An embodiment of the invention which is especially advantageous with respect to an especially compact and functionally reliable configuration of the dosage counting device is provided in that the switching finger, the actuation portion and the arm part extend substantially arc-shaped about the rotational axis of the first counting ring. The radius of this arc corresponds advantageously substantially to half the diameter of the shoulder formed on the dispensing container. In this way, it is advantageously possible to arrange the counting ring switching device directly in the area of the dispensing valve of the inhalator. In this way, it is advantageously possible to form a housing portion provided for guiding the dispensing container of the inhalator by a separately formed tubular element which is placed onto the mouthpiece of the inhalator.

An advantageous embodiment of the invention with respect to a reliable counting of the individual dosage strokes is provided in that a reverse motion check device is provided which has a locking pawl which engages, at least upon further transport of the first counting ring by one counting step, a correspondingly formed engagement portion provided on the counting ring.

As an alternative, or also in combination with such a locking pawl, it is also possible to prevent rotation of the first counting ring counter to the counting ring switching direction by a frictional locking mechanism. The counting ring switching device; and, advantageously, also the reverse motion check device are formed according to a special aspect of the present invention such that they count each dispensing or dosage stroke.

In an advantageous way, the switching mechanism is formed such that the first counting ring is actuated and rotated farther even when a dispensing stroke has been performed only incompletely. An advantageous embodiment of the invention with respect to an especially easy-running configuration of the reverse motion check device is provided in that several locking pawls are provided which can be brought into engagement with corresponding engagement portions formed on the first counting ring, wherein the individual locking pawls are arranged in a staggered arrangements to one another such that these locking pawls are each in different engagement states.

The length of the arm part and the length of the switching fingers as well as the position of the arm part and of the switching finger are adjusted such that upon displacement of the actuating element by a predetermined travel stroke the engagement portion of the switching finger is displaced in the circumferential direction of the first counting ring by a travel distance whose length is substantially identical to the step length of a scale provided at the periphery of the first counting ring. In this way, it is possible advantageously to display the number combination required for the indication of each individual counting step in a uniquely defined way.

An advantageous embodiment of the invention with respect to an especially reliable counting and indication of the individual dosage strokes is provided in that the scale of the first counting ring has the numbers of 0, 1, 2 . . . to 9, wherein these numbers are provided with identical peripheral division on the periphery of the first counting ring. These numbers can be, for example, applied by screen printing onto the counting ring. However, according to an especially preferred embodiment of the invention, the scale is burned by means of a laser writing method directly into the plastic material of the counting ring.

Also, the scale of the second counting ring has in an advantageous manner the numbers 0, 1, 2 . . . to 9. The application of the numbering of the second counting ring can be carried out in the same way as explained above with respect to the first counting ring.

An advantageous embodiment of the invention with respect to counting a comparatively large number of strokes is provided in that the scale of the second counting ring has the numbers 0, 1, 2 . . . to 20. In this way it is advantageously possible to count with only two counting rings a total of 200 dosage strokes. In particular, in this embodiment on the first counting ring the series of numbers 0, 1, 2 . . . to 9 is arranged several times in sequence, in particular, 2 to 3 times. This shortens considerably the transport distance for further switching of the first counting ring.

The coupling device for coupling the second counting ring with the first counting ring for a step-wise rotation of the second counting ring together with the first counting ring comprises advantageously a tongue which is formed on the first counting ring and which is elastically deflectable and can be brought into direct engagement with an engagement portion of the second counting ring. This tongue is deflected according to a preferred embodiment of the invention by a contact nose that is stationarily arranged relative to the first counting ring which maintains the elastically deflectable tongue in engagement with the second counting ring across an angle interval which corresponds exactly to the step angle for further switching of the second counting ring. For realizing corresponding gear ratios, if needed, several such contact noses can be formed on a component of the inhalator which is stationarily arranged relative to the first counting ring. If needed, it is also possible to form several elastically deflectable tongue elements on the first counting ring which are designed to be brought into direct contact with the second counting ring.

An advantageous embodiment of the inhalator with respect to an especially reliable operation of this coupling device is provided in that the second counting ring comprises a bearing portion which is inserted into the first counting ring so as to be rotatable or is placed onto the first counting ring. By providing corresponding circumferential grooves and engagement portions between the two counting rings, it is possible to support the two counting rings so as to be rotatable relative to one another and to prevent an axial pulling-apart of the two counting rings. The position of the first counting ring relative to the contact noses can be maintained in an advantageous way by a circumferential groove provided on the first counting ring.

The rotation of the second counting ring counter to the switching direction is advantageously prevented by an additional reverse motion check device.

BRIEF DESCRIPTION OF THE DRAWINGS

Further details and features of the invention result from the following description of a preferred embodiment in connection with the drawing. It is shown in:

FIG. 1 a longitudinal sectional view of an inhalator with mouthpiece and displaceably arranged dispensing container, FIGS. 2a, 2b, and 2c a schematic representation for illustrating the transport mechanism of the counting ring switching device provided in the inhalator according to FIG. 1, FIGS. 3a and 3b a schematic illustration for a more detailed description of a preferred geometry of the switching finger, an actuation portion, and an arm portion, FIGS. 4a, 4b, and 4c axial sectional views of the first and the second counting rings for explaining the function of the coupling device for direct coupling of the first and second counting rings, FIG. 5 a longitudinal section of a cover portion with integrated switching finger as well as integrally formed reverse motion check device, FIG. 6 a radial section view along the line A—A in FIG. 5 for explaining the configuration of the reverse motion check device, and FIG. 7 a simplified side view of the inhalator according to FIG. 1 with a substantially rectangularly formed reading window aligned along the longitudinal axis of the inhalator.

DESCRIPTION OF PREFERRED EMBODIMENTS

Figure 1:
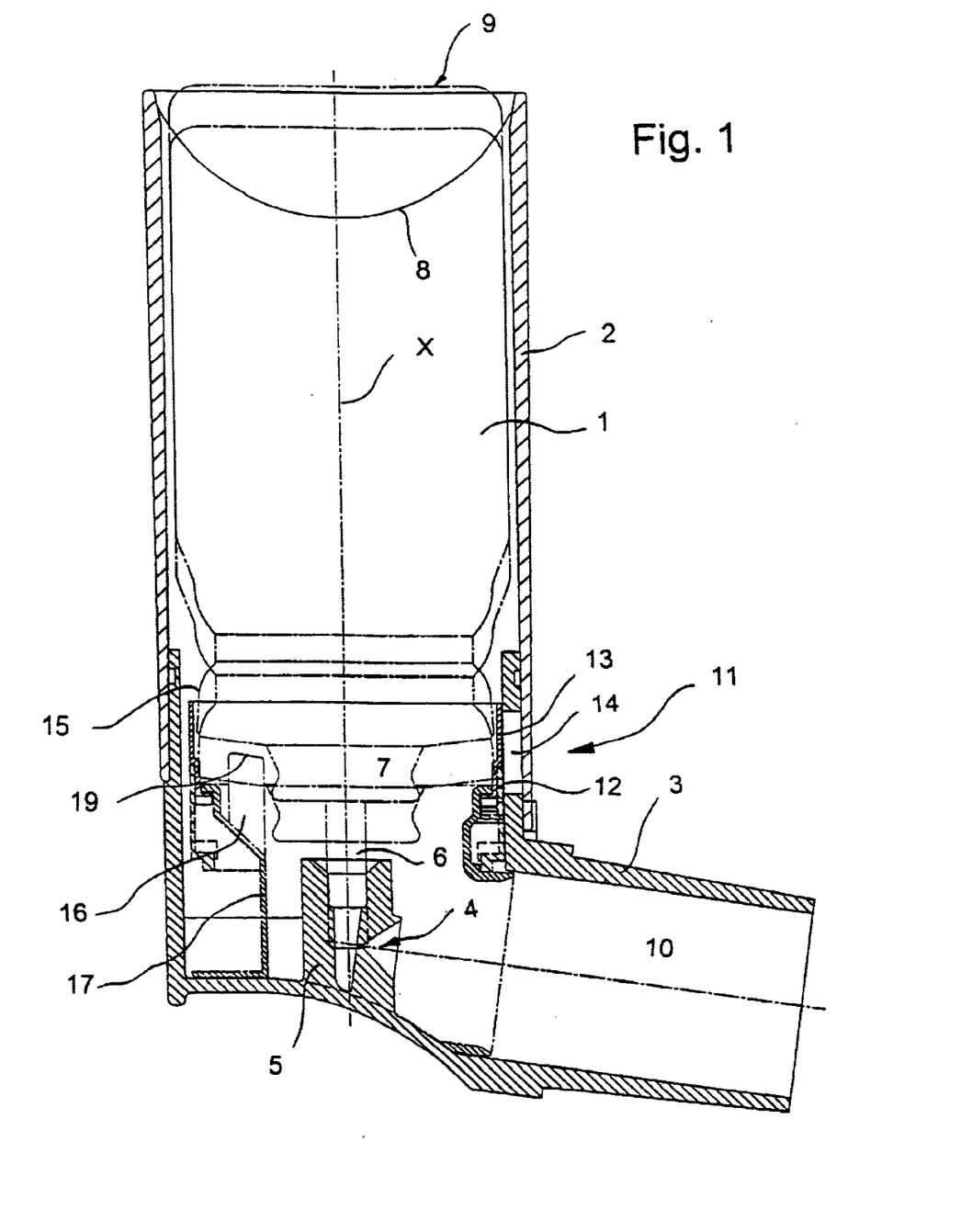

The inhalator illustrated in a simplified way in FIG. 1 for dispensing an aerosol comprises a dispensing container 1 slidably arranged along an axial direction and the guiding shaft 2 provided for supporting the dispensing container 1 which is placed in a fitting way onto a correspondingly formed connecting portion of an angular member 3.

A spray nozzle device 4 is arranged in the angular member 3 and is formed in a pin portion 5 formed as a monolithic part of the angular member 3. In this pin portion 5 a dispensing tube 6 of the dispensing container 1 is inserted in a sealed fashion. The dispensing tube 6 is received yieldingly in the axial direction in the head area 7 of the dispensing container 1 and is pre-tensioned by a spring device (not visible) such that the dispensing container 1 is forced via the dispensing tube 6 away from the pin portion 5.

In the upper area of the guide shaft 2 a depression 8 is provided from which a bottom portion 9 of the dispensing container 1 projects. By applying a pressure force onto this bottom area 9, the dispensing container 1 can be moved toward the pin portion 5 as is indicated by the dash-dotted line in a simplified fashion. As soon as the dispensing tube 6 contacts the contact surface formed correspondingly on the pin portion 5, the dispensing tube 6 is forced into the dispensing container 1 and cooperates with a valve mechanism via which a pre-determined amount of the medium stored in the dispensing container 1 can flow out of the container and can flow via the dispensing tube 6 and the spray nozzle device 4 and from there into a intake area 10 formed in the angular member 3. This insertion movement, which is referred to in the following as dispensing stroke, of the dispensing container 1 is counted by a dosage counting device 11.

The dosage counting device 11 comprises for this purpose a first counting ring 12 and a second counting ring 13. The first counting ring 12 and the second counting ring 13 are rotatably arranged relative to one another. The second counting ring 13 has a rotational bearing portion which is inserted into a corresponding opening area of the first counting ring 12.

The first counting ring 12 and the second counting ring 13 are arranged coaxially relative to the longitudinal axis X of the dispensing container 1. The two counting rings 12, 13 are rotationally arranged in a tubular portion of the angular member 3. On the outer circumferential surface of the two counting rings 12, 13, numbers are provided in a way which will be explained in the following in more detail which numbers can be read via a window opening 14 which is formed in the angular member 3.

The embodiment of the inhalator illustrated in FIG. 1 has a second counting ring arranged approximately at the level of the shoulder 15 formed on the receiving container 1. The second counting ring 13 is sized with respect to its inner diameter such that the shoulder 15 of the dispensing container 1 can penetrate by a travel stroke, corresponding to the dispensing stroke length, into the second counting ring 13.

In an annular space provided between the two counting rings 12, 13 and the head area 7 of the dispensing container, a counting ring switching device 16 is provided which rotates the counting ring 12, arranged coaxially to the dispensing container 1, by a certain angular distance for each dispensing stroke.

The counting ring switching device 16 is formed in the illustrated embodiment as a monolithic part of the cover portion 17 which is inserted into the angular member 3. The cover portion 17 forms a bearing portion which extends substantially annularly about the longitudinal axis X on which the second counting ring 13 is supported.

On the cover portion 17 a reverse motion check device for locking the rotational movement of the counting rings 12, 13 in the counter direction is provided as a monolithic part, respectively. The cover portion 17 is furthermore provided with a contact nose which forms part of a coupling device, to be explained in the following, for direct coupling of the two counting rings 12, 13.

The counting ring switching device is arranged within the two counting rings 12, 13 such that an actuation portion 19 thereof can be brought into contact with the shoulder provided on the dispensing container 1.

The function of the counting ring switching device will be explained with the aid of the FIGS. 2a, 2b, 2c. The counting ring switching device 16 illustrated in FIGS. 2a, 2b, and 2c comprises a gear member, referred to in the following as a switching finger 20. In the illustrated embodiment, it is coupled by the actuation portion 19 with an arm part 21. In the illustrated embodiment, the switching finger 20, the actuation portion 19, and the arm part 21 are formed together as a monolithic part, and, as a result of the own elasticity of the plastic material employed here, they are moveably coupled with one another.

The arm part 21 has a stationary end facing away from the actuation portion 19 by which the entire joint mechanism, formed by the arm part 21, the actuation portion 19, and the switching finger 20, is supported in the circumferential direction of the first counting ring 12.

In the illustrated arrangement, the arm part 21 and the switching finger 20 form an elbow joint mechanism. By a gradual suppression of the actuation portion along the indicated longitudinal axis X of the dispensing container 1, the arm part 21 and the switching finger 20 are pivoted gradually into the final position illustrated in FIG. 2. Relative to a projection surface perpendicular to the axis X a displacement results between the projection of the position of the movable end of the arm part 21 with respect to the projection of the position of this end in the end position. According to this displacement, the actuation portion is moved in the circumferential direction of the first counting ring. Also, the switching finger 20 is pivoted upon suppression of the actuation portion so that, as a whole, in this connection an elongation of the projection of the switching finger 20 in the projection surface perpendicular to the aforementioned longitudinal axis X results. Since the switching finger 20 with the end portion facing away from the first counting ring 12 is also coupled with the actuation portion, an addition of the displacement strokes, achieved by pivoting of the arm part and of the switching finger 20, results. For transmitting the corresponding movement component, acting in the circumferential direction of the first counting ring, onto the first counting ring, the switching finger 20 is provided with an engagement portion 22 which can be brought into engagement with the control elements formed on the counting ring. By a corresponding movement of the engagement portion 22 of the switching finger 20 in the circumferential direction of the first counting ring 12, the first counting ring 12 is transported in the circumferential direction by a predetermined travel stroke as a result of the engagement with the control elements 23. This predetermined travel stroke corresponds substantially to the spacing between the two neighboring control elements 23. Since the actuation portion 19 is moved into a lower end position as a result of the shoulder of the dispensing container 1, the actuation portion 19, as a result of the own elasticity of the arm part 21, will also spring back into its initial position upon return movement of the dispensing container 1 in the guide shaft 2. During this return movement the switching finger 20, respectively, its engagement portion, bypass the control element 23, which will come into contact with the latter during the subsequent counting stroke, and springs directly behind this control element 23 again into its engagement position. Upon a new suppression of the actuation portion 19, the engagement portion 22 of the switching finger moves the control element 23, formed on the first counting ring, again by a transport interval in the circumferential direction. The number which is the successively arranged one on the circumferential surface of the first counting ring 12 now is moved into the window opening 14.

Figure 2A:
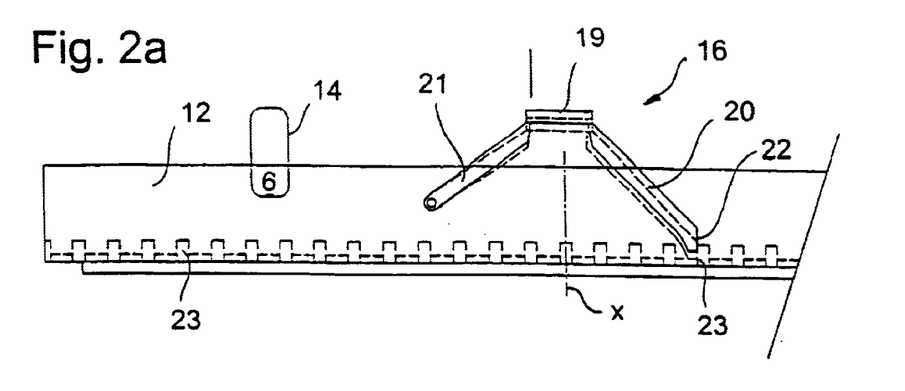
Figure 2B:
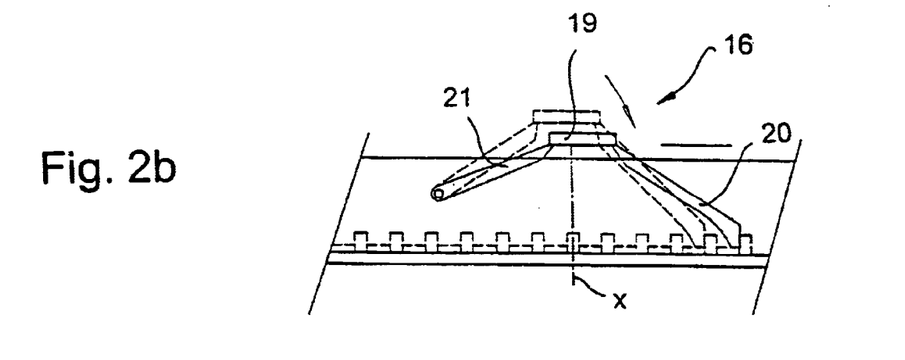
Figure 2C:
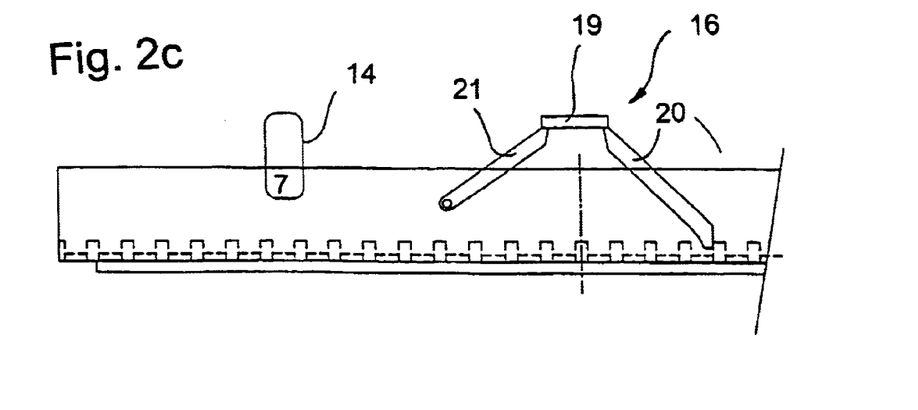

In the illustrations according to FIGS. 2a, 2b, 2c the counting ring switching device for switching the first counting ring is illustrated in a developed illustration.

Figure 3A:
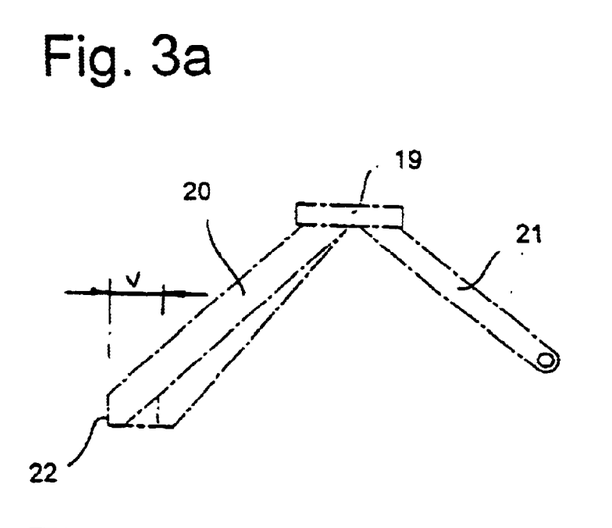
Figure 3B:
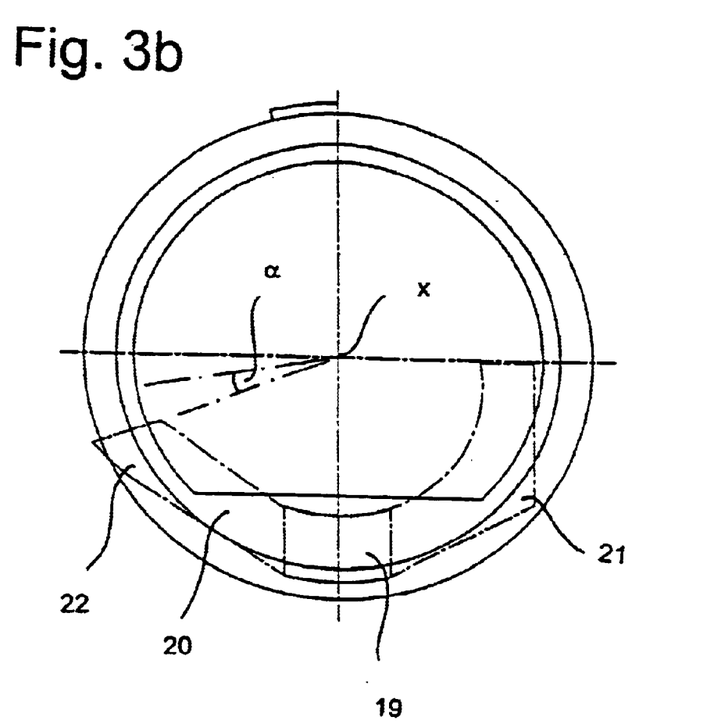

In the embodiment illustrated in FIG. 1, the joint mechanism formed by the arm part 21, the actuation portion 19, and the switching finger 20 of the counting ring switching device, extends, as illustrated in FIG. 3b, substantially arc-shaped about the longitudinal axis X of the dispensing container 1 (not illustrated in FIG. 3). By suppressing the actuation portion 19 illustrated in FIG. 3b a displacement of the engagement portion 22 of the switching finger 21 in the circumferential direction is achieved. As a result of the displacement of the engagement portion 22 of the switching finger 20 in the circumferential direction, the first counting ring 12 can rotate farther by a switching angle a in the circumferential direction. In the case that on the outer circumference of the first counting ring 12 three number sequences of the numbers 0 to 9 are provided, the switching angle α is approximately 12°. For such a switching angle, a sufficiently large spacing between the neighboring numbers results for a diameter of the first counting ring 1 corresponding to the diameter of the dispensing container 1 so that an easy readability of the individual numbers in the window opening 14 is ensured. The gear ratio between the first counting ring 12 and the second counting ring 13 is determined in correspondence to the number of the number sequences provided on the circumference of the first counting ring 12. The required gear ratio between the two counting rings can advantageously be achieved by the coupling device described in the following in connection with FIGS. 4a, 4b, 4c.

Figure 4A:
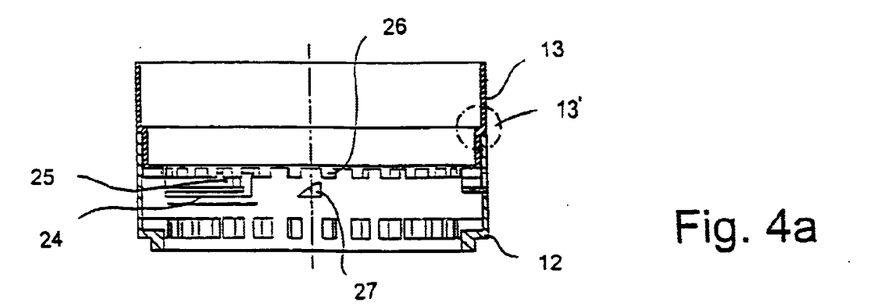
Figure 4B:
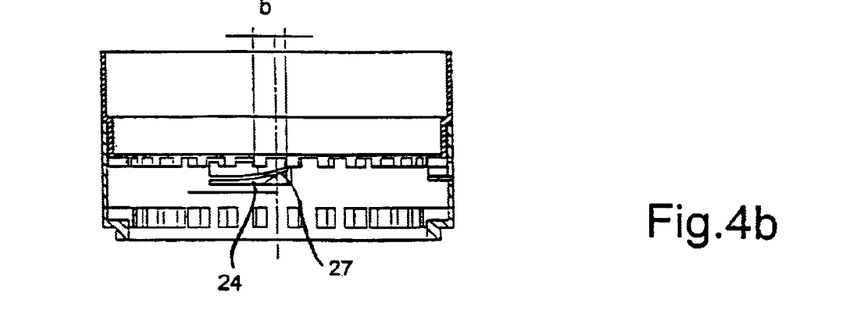
Figure 4C:
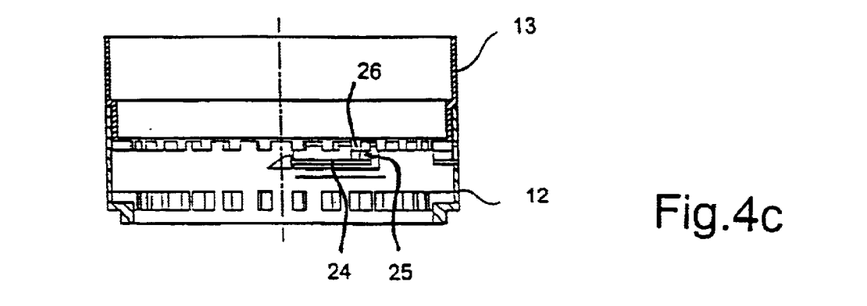

The coupling device illustrated in different coupling states in FIGS. 4a, 4b, 4c comprises a tongue element 24 which is formed as a unitary part of the first counting ring 12. In the illustration according to FIG. 4a it is in a neutral position. A follower portion 25 is formed on the tongue element 24. This follower portion 25 is designed to engage engagement projections 26 which are formed as a monolithic part with the second counting ring 13. In this connection, a contact nose 27 provided on the cover portion 17 is provided which forces the tongue element into a coupling position in which the follower portion 25, provided on the end of the tongue element 24, engages the engagement projections 26 of the second counting ring 13 positioned directly adjacently. As soon as a corresponding engagement state is produced, the second counting ring 13 is rotated together with the first counting ring 12 until the tongue element 24 drops off the contact nose 27 so that the engagement state between the follower portion 25 and the corresponding engagement projection 26 is canceled. As soon as this engagement state is canceled, the first counting ring 12 can be further moved by a certain travel stroke, independently of the second counting ring 13.

In FIG. 4b the tongue element 24 is forced into the aforementioned coupling position by the contact nose 27, not visible in this illustration. The length of the coupling stroke, identified by the letter b, is determined by the geometry of the contact nose 27.

In FIG. 4c the tongue element 24 is already returned into its initial position and the engagement between the follower portion 25 and the corresponding engagement projection 26 of the second counting ring 13 is cancelled.

The tongue element 24 provided in the illustrated embodiment is a monolithic part of the first counting ring 12 and is formed as a substantially flat leaf spring element. With respect to the required mechanical properties of the tongue element as well as with respect to an especially high precision fit of the first counting ring 12, it is preferably made of POM plastic material. In the here illustrated embodiment, the numbers 1 to 20 are arranged at the outer circumferential surface of the second counting ring 13. By means of the two counting rings 12, 13, 200 dosages can be individually counted in this embodiment. With the two counting rings it is possible to provide counting up to 999. By employing a third counting ring, a count up to 9,999 is possible. The coupling device for coupling a third counting ring with the second counting ring corresponds in its design advantageously to that between the first counting ring 12 and the second counting ring 13.

For preventing a rotational movement of the second counting ring 13 relative to the first counting ring 12 counter to the transport direction, determined by the coupling device 24, 25, 26 as well as the contact nose 27, a reverse motion check device 29 is provided for the counting rings 12 and 13 which can be brought into engagement with corresponding catch portions. In the here illustrated embodiment, these catch portions of the reverse motion check device are formed in a simple way by the engagement projections 23 and 26.

Figure 5:
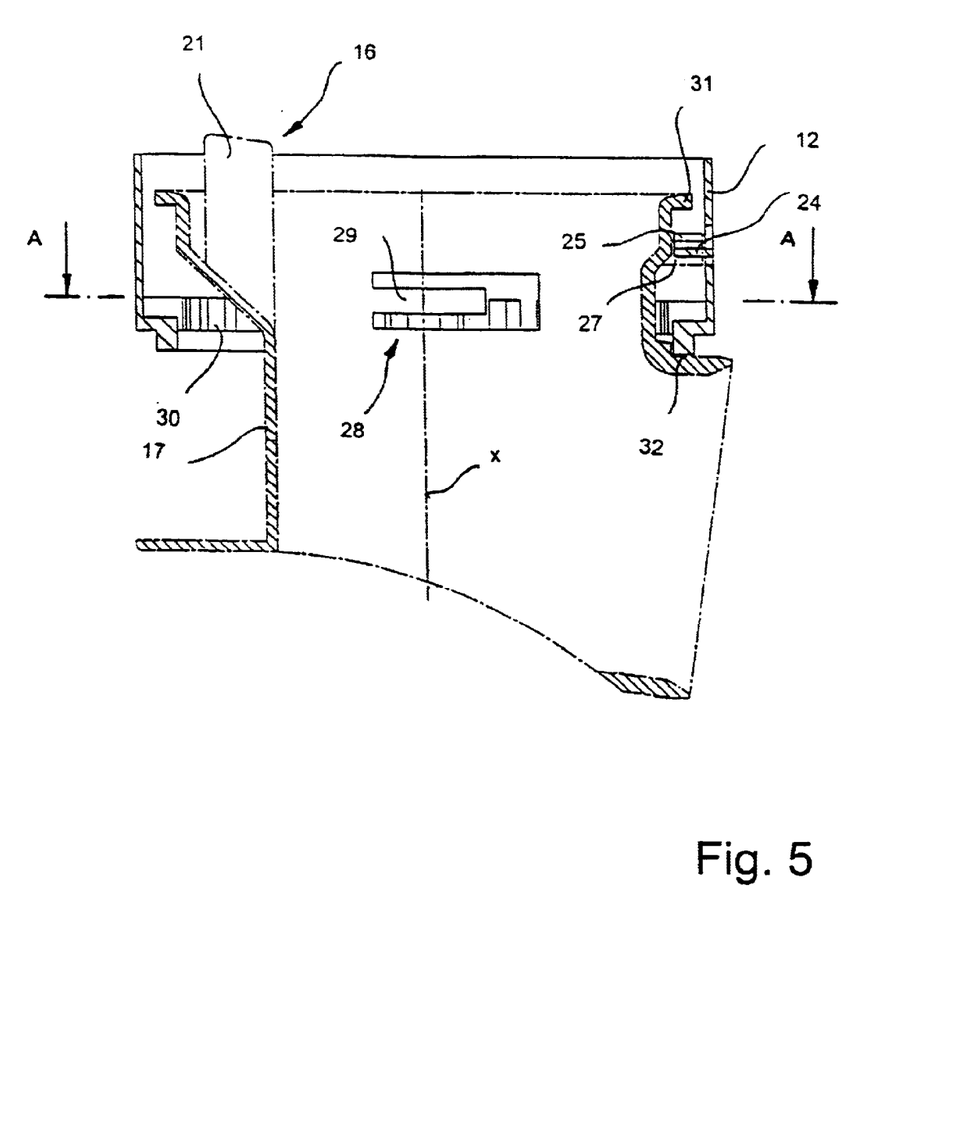
Figure 6:
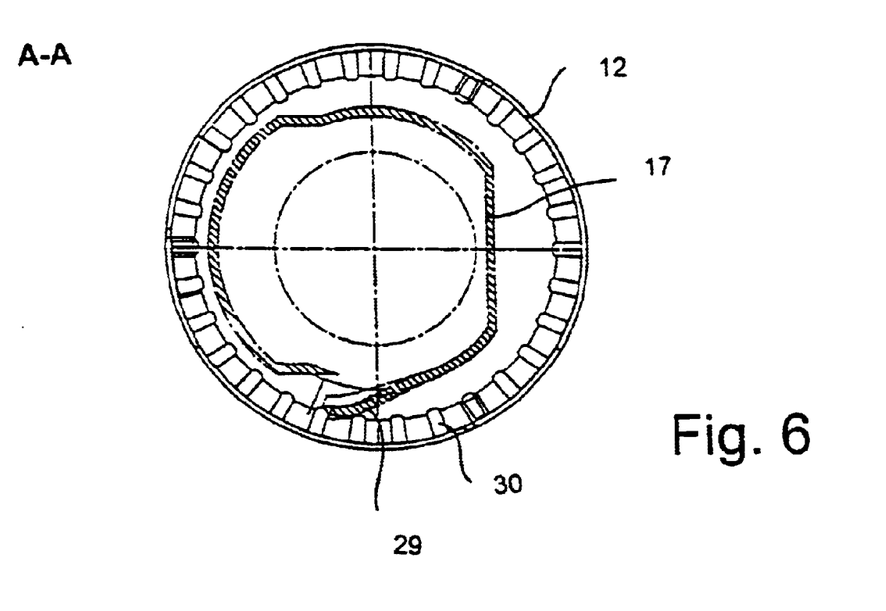

In FIG. 5 the cover portion 17 provided for the inhalator according to FIG. 1 and the first counting ring 12 placed thereon are illustrated on an enlarged scale. In the shown embodiment,, the reverse motion check device 28, provided for preventing rotational movement of the first counting ring 12 counter to the counting ring switching direction, comprises a spring element 29 formed, as a monolithic part of the cover portion 17 which can engage catch projections 30 which are formed on the inner circumference of the first counting ring 12 and face the counting ring rotational axis X. The special geometry realized in this embodiment of the spring element formed as a monolithic part of the cover portion 17 can be seen in FIG. 6 showing a simplified radial sectional view along the line A—A.

As can be seen also in the illustration according to FIG. 5, the tongue element 24, which is provided for direct further rotation of the second counting ring 13 (not illustrated), has a flat rectangular cross-section and projects from an inner circumferential wall of the first counting ring 12 into an annular space provided between the first counting ring 12 and the cover portion 17. This annular space is limited in its upper area by a contact portion 31 which supports the second counting ring 13, not illustrated here, in the axial direction. The illustrated,cover portion 17 forms moreover a second contact portion 32 by which the first counting ring 12 is supported in the axial direction. With respect to the fact that the first and second counting rings 12, 13 are supported against one another in the axial direction as a result of the shoulder structure illustrated in FIG. 1, the two counting rings 12, 13 are as a whole supported in the axial direction by the aforementioned first and second contact portions 31 and 32.

In the sectional view according to FIG. 5, the contact nose 27 provided for deflecting the follower portion 25 provided on the end portion of the tongue element 24 is shown only in dash-dotted lines. The counting ring switching device 16, provided as a unitary part of the cover portion 17, and, in particular, its arm part 21, are also shown only in dash-dotted lines.

The configuration of the mentioned filigree structure of a cover portion, insertable into the main housing portion of the inhalator, is advantageous with respect to manufacturing-technological aspects. However, it is principally also possible to eliminate the cover portion 17 and to embody the reverse motion check device 28 for locking the reverse movement of the first counting ring 12 as well as the counting ring switching device and the corresponding support portions for supporting the first and second counting rings 12, 13 directly on, i.e., as a monolithic part of, the angled member 3.

The division of the catch projections 30 provided on the first counting ring 12, illustrated in a sectional view according to FIG. 6, is pre-determined such that the reverse motion check device locks the first counting ring 12 anew after each counting step by means of the spring element 23. With a corresponding reduction in size of the catch projections 30 and reduction in size of the spacing between the successively arranged catch projections it is possible to make the catch intervals of the reverse motion check device smaller and to thus prevent a rotational movement of the first counting ring even when the first counting ring 12 is not rotated by a complete counting step. With a corresponding configuration of the geometry of the spring element 29, the rotational resistance generated by the reverse motion check device 28 can be maintained at a comparatively minimal value.

Figure 7:
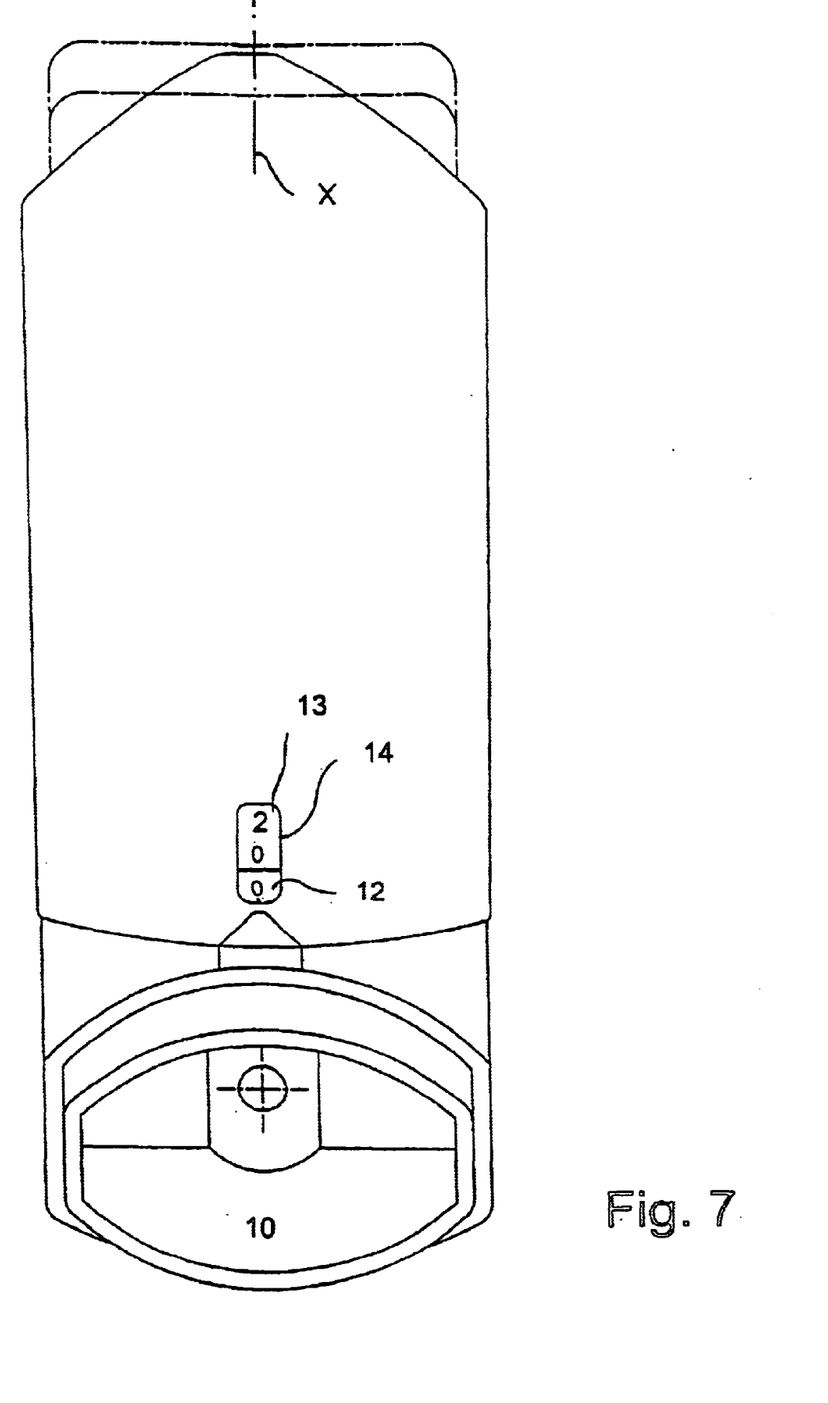

In FIG. 7 a side view (side view from the right) of the inhalator illustrated in FIG. 1 is shown. The window opening 14 arranged on the side of the intake area 10 shows the number display. "200". This number display is provided when by means of the first counting ring 12 the number "0" has been positioned in the window opening 14 and by means of the second counting ring 13 the number "20" has been moved into the window opening. For example, in the case of a descending count, the first counting ring 12 as well as the second counting ring 13 are rotated farther by an angular interval (α) about the longitudinal axis X of the inhalator upon the next actuation of the inhalator. Accordingly, via the first counting ring 12, the number "9" and via the second counting ring 13 the number "19" reach the window opening 14. Accordingly, in the window opening 14 the number "199" is shown. Upon subsequent actuation of the inhalator, the first counting ring 12 is now further rotated and the number "8" is positioned in the window opening 14. The window opening 14 now shows the number "198". In connection with the following dosage strokes, first the; first counting ring 12 is further rotated by single counting steps, respectively, until the number "1" enters the window opening 14 and in the window opening 14 the number "191" is shown. Upon the next actuation of the inhalator, as a result of the coupling mechanism illustrated in FIGS. 4a to 4c, the first counting ring 12 is directly coupled with the second counting ring and the first counting ring 12 together with the second counting ring 13 are further rotated by one counting step. Accordingly, the number 0 provided on the periphery of the first counting ring and the number "19" at the periphery of the second counting ring 13 are positioned in the window opening 14. In the window opening 14 the number "190" is now shown. As soon as the number "19" has reached completely the window opening 14, the coupling mechanism for the direct coupling of the first and second counting ring 12, 13 is returned into its release position and the first counting ring 12 during the next dosage strokes is rotated independently of the second counting ring 13 until the number "1" of the first counting ring 12 again reaches the window opening 14.

In order to provide a substantially identical division of the number sequence on the first counting ring 12 and the second counting ring 13, the number sequence of 0 to 9 is provided twice on the outer circumference of the first counting ring 12. For a more narrow design of the window opening 14 relative to the circumferential direction of the counting rings, on the second counting ring 13, for example, the numbers 0 to 40 can be provided. With a corresponding adjustment of the gear ratio between the first and the second counting ring 12, 13, for example, by multiplying the number of contact noses 27, provided for further transport of the second counting ring, numbers of 0 to 400 can be counted in a descending or ascending sequence with only two counting rings.

The invention is not limited to the aforementioned embodiments. For example, it is also possible to eliminate the cover portion 17 provided in the afore described preferred embodiment of the inhalator and to form the corresponding functional parts integrally with the housing of the inhalator. If needed, aerosol-free active substances can also be dispensed with the described inhalator. For making available an even larger counting range, it is possible to provide a third counting ring which can be coupled by a corresponding coupling mechanism with the second counting ring.

What is claimed is:

1. The inhalator for dispensing an aerosol, comprising:
    a dosage counting unit (11),
    a housing device (2,3) having a stationary part (17),
    an aerosol dispensing container (1) arranged in the housing device (2, 3) and slidable relative to the housing device (2, 3) in a direction of a longitudinal axis of the aerosol dispensing container (1),
    a first counting ring (12) arranged coaxially to the longitudinal axis (X) of the aerosol dispensing container (1) and rotatable about the longitudinal axis (X),
    a second counting ring (13) arranged coaxially to the first counting ring (12) and rotatable relative to the first counting ring (12),
    a counting ring switching device (16) for rotating the first counting ring (12) upon actuation of the inhalator,
    a coupling device (24, 25, 26, 27) coupling the second counting ring (13) to the first coupling ring (12) for a stepwise rotation by a counting step of the second counting ring (13) together with the first counting ring (12),
    wherein the counting ring switching device (16) has an actuation portion (19) and a switching finger (20) coupled to the actuation portion (19),
    wherein the first counting ring (12) has control elements (23),
    wherein the switching finger (20) engages the control elements (23) for rotation of the first counting ring (12) in a counting direction, and
    wherein the switching finger (20) is spaced from the longitudinal axis (X) and is arranged at a slant to the longitudinal axis (X) and engages the control elements (23) axially, further comprising
        an elastically yielding arm part (21) coupled with the switching finger (20) via the actuating portion (19) such that the arm part (21) and the switching finger (20) form an elbow joint mechanism, the arm part (21) being supported on the stationary part (17).

2. The inhalator according to claim 1, wherein the switching finger (20) has an engagement portion (22) and is configured to be deflected from an initial position into an end position slanted relative to the initial position, wherein in the initial position the engagement portion of the switching finger (20) is elastically yieldingly forced into an engagement position with the first counting ring (12).

3. The inhalator according to claim 1, wherein the arm part (21) and the switching finger (20) are connected to one another by the actuation portion (19).

4. The inhalator according to claim 1, wherein the arm part (21) and the switching finger (20) are formed as a monolithic part.

5. The inhalator according to claim 1, wherein the arm part (21) and the switching finger (20) are comprised of a plastic material.

6. The inhalator according to claim 1, wherein the actuation portion (19) is guided in a direction substantially parallel to a rotational axis of the first counting ring (12) and wherein the arm part (21) forms a spring element forcing the switching finger (20) into the initial position.

7. The inhalator according to claim 1, wherein the aerosol dispensing container (1) has a shoulder and wherein the actuation portion (19) has a contact surface configured to contact the shoulder of the aerosol dispensing container (1).

8. The inhalator according to claim 1, wherein the switching finger (20), the actuation portion (19), and the arm part (21) extend substantially arc-shaped about a rotational axis (X) of the first counting ring (12).

9. The inhalator according to claim 1, further comprising a reverse motion check device (28) for preventing a rotational movement of the first counting ring (12) counter to the counting direction.

10. The inhalator according to claim 9, wherein the reverse motion check device (28) has a locking pawl.

11. The inhalator according to claim 1, further comprising a first scale provided circumferentially on the first counting ring (12), wherein a length of the arm part (21), a length of the switching finger (20), and a position of the arm part (21) and a position of the switching finger (2a) are adjusted such that upon a displacement of the actuating element (19) by a predetermined travel distance the engagement portion (22) of the switching finger (20) is displaced in a circumferential direction of the first counting ring (12) by a travel distance having a length matching a step length of the first scale.

12. The inhalator according to claims 11, wherein the first scale has a number sequence 0, 1, 2 . . . to 9.

13. The inhalator according to claims 11, further comprising a second scale provided on the second counting ring (13), wherein the second scale has the numbers 0, 1, 2, . . . to 9.

14. The inhalator according to 11, further comprising a second scale provided on the second counting ring (13), wherein the scale of the second counting ring (13) has the numbers 0, 1, 2, . . . 9, 10, 11, . . . 19 and 20.

15. The inhalator according to claim 12, wherein the number sequence 0, 1, . . . 9 is provided multiple times.

16. The inhalator according to claim 1, wherein the second counting ring (13) has a bearing portion rotatably inserted into the first counting ring (12).

17. The inhalator according to claim 1, wherein the second counting ring (13) has a bearing portion placed onto the first counting ring (12).

18. The inhalator according to claim 1, wherein the coupling device (24, 25, 26, 27) has a follower element coupled with the first counting ring (12).

19. The inhalator according to claim 18, wherein the follower element is formed by an elastically yielding tongue element (24) formed as a monolithic part of the first counting ring (12).

20. The inhalator according to claim 19, wherein the coupling device has at least one stationary contact nose (27)

for deflecting the tongue element (24) such that the tongue element engages the second counting ring (13) over a circumferential length corresponding to the counting step and rotates the counting ring (13) by the circumferential length.

21. The inhalator according to claim 20, wherein the second counting ring (13) has a toothing portion configured to engage the tongue element (24).

22. The inhalator according to claim 20, wherein three of the stationary contact noses (27), spaced uniformly from one another in the circumferential direction, are provided such that the second counting ring (13), upon a complete circumferential revolution, entrains the second counting ring (13) by three counting steps.

* * * * *